United States Patent [19]

Nemet-Mavrodin et al.

[11] 4,400,558
[45] Aug. 23, 1983

[54] RECOVERY OF 2-PHENYLETHANOL

[75] Inventors: Margaret I. Nemet-Mavrodin, Robbinsville; John F. White, Princeton, both of N.J.

[73] Assignee: Atlantic Richfield Company, Los Angeles, Calif.

[21] Appl. No.: 255,011

[22] Filed: Apr. 17, 1981

[51] Int. Cl.$^3$ ............................................. C07C 29/88
[52] U.S. Cl. .................................. 568/810; 568/815; 568/569; 568/320; 549/532
[58] Field of Search ............................. 568/810, 815

[56] References Cited

U.S. PATENT DOCUMENTS 2,114,286  4/1938  Britton ................................. 568/810
3,947,501  3/1976  Kollar .................................. 568/810
4,359,365  11/1982  Deguchi et al. ................. 568/810 X

FOREIGN PATENT DOCUMENTS 54-3026  1/1979  Japan .................................. 568/810

Primary Examiner—Bernard Helfin
Attorney, Agent, or Firm—Atlantic Richfield Company

[57] ABSTRACT

The present invention provides a novel method for recovering 2-phenylethanol which is produced as a by-product of non-catalytic air oxidation of ethylbenzene, and as a by-product, in the ethylbenzene hydroperoxide epoxidation of an olefinically unsaturated compound, e.g., propylene, to the corresponding alkylene oxide, e.g., propylene oxide. In such processes, 2-phenylethanol accumulates in a process stream typically comprising major proportions of methylbenzyl alcohol, ethylbenzene, alkylene oxide and acetophenone. Conventional distillation-separation procedures may remove most of the alkylene oxide and ethylbenzene, leaving a process stream which is eventually used for styrene monomer production which contains minor amounts, i.e., less than about 20 weight percent, of 2-phenylethanol. The present invention provides a novel method of recovering 2-phenylethanol from that process stream prior to its conversion to other by-products in the dehydration and hydrogenation steps which are utilized to produce styrene monomer. The present invention provides a 2-phenylethanol removal method comprising the preparation of a 2-phenylethanol feed stream having a methylbenzyl alcohol concentration of between about 10 and 70 weight percent, and a 2-phenylethanol concentration of between about 20 and 80 weight percent. This prepared feed stream is then diluted with an organic diluent, such as ethylbenzene, and is subjected to a metal halide addition which results in the formation of an insoluble 2-phenylethanol metal halide complex which is separated, washed and decomposed to produce a crude 2-phenylethanol product, which may be distilled to remove residual diluent to provide a high purity 2-phenylethanol product exhibiting superior fragrance qualities.

16 Claims, 3 Drawing Figures

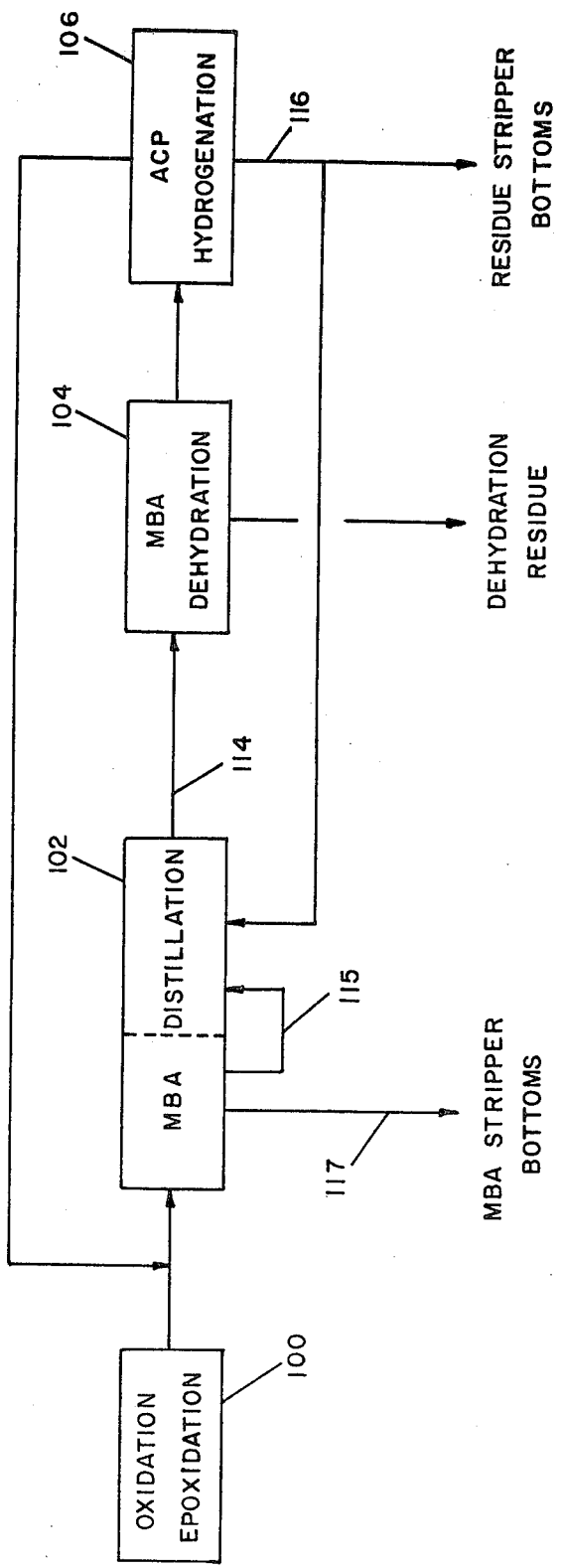
FIGURE 1: SOURCE OF 2-PHENYLETHANOL IN COPRODUCTION OF PROPYLENE OXIDE AND STYRENE MONOMER PROCESS

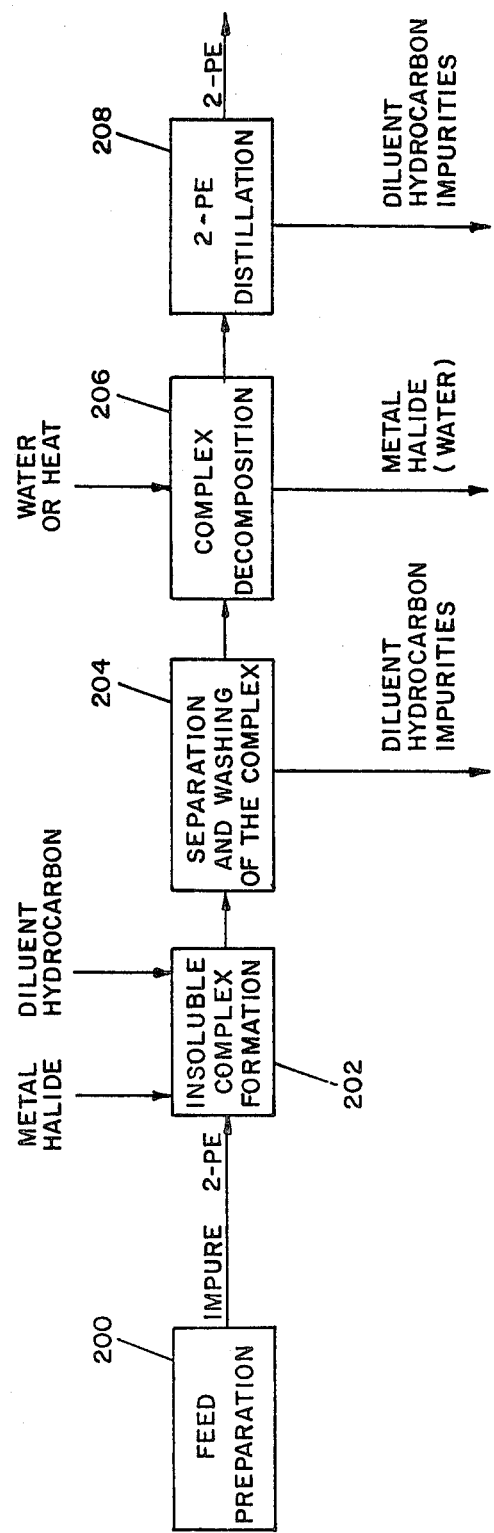
FIGURE 2: CONCEPTUAL FLOW DIAGRAM OF 2-PE PURIFICATION BY COMPLEXATION WITH METAL HALIDES

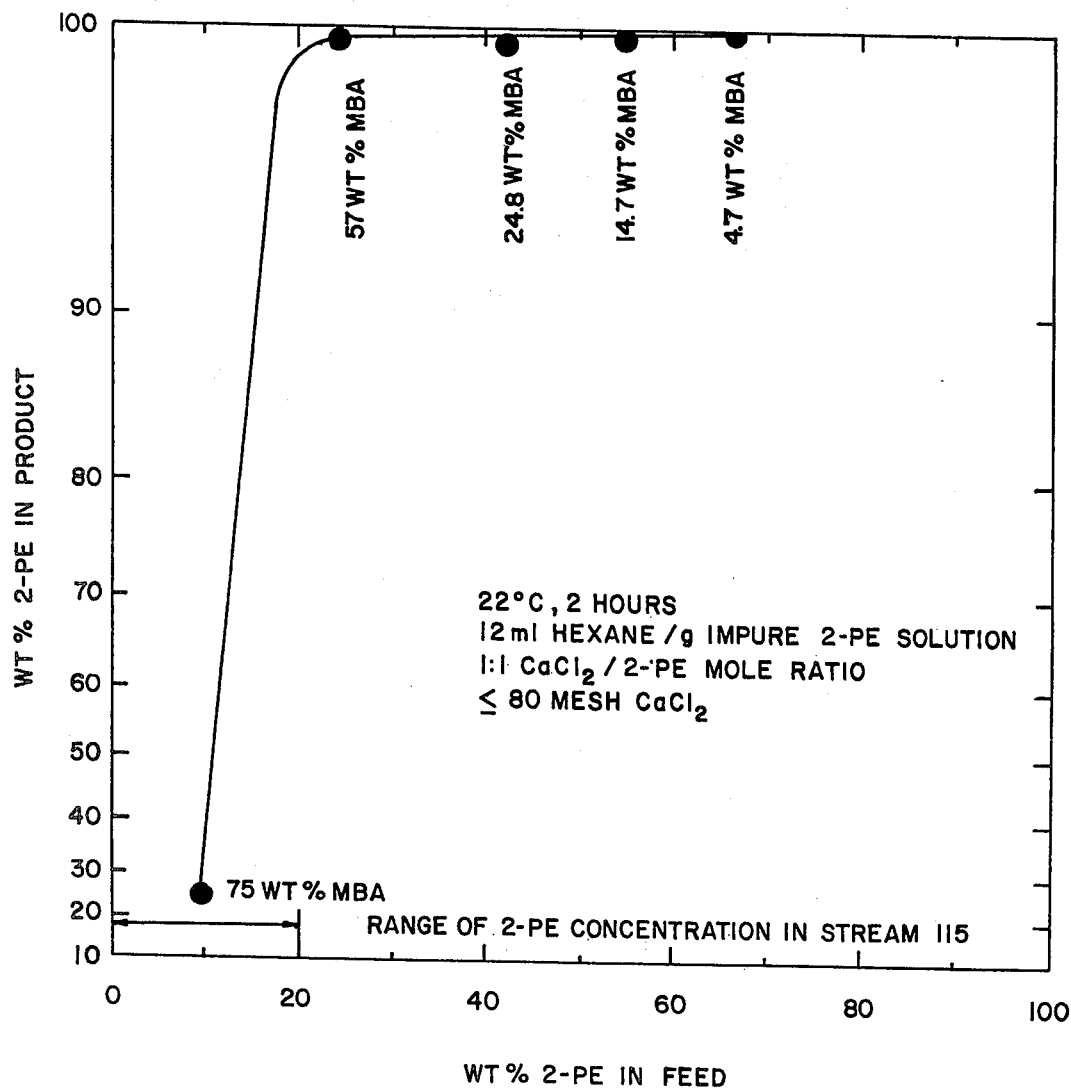
FIGURE 3: EFFECT OF MBA CONCENTRATION IN THE FEED TO 2-PHENYLETHANOL COMPLEXATION ON SELECTIVITY

RECOVERY OF 2-PHENYLETHANOL

BACKGROUND OF THE INVENTION

A. Field of the Invention

The present invention relates generally to the field of alkylene oxide-styrene monomer production processes, and more particularly to methods for recovering and refining by-products resulting from those processes. The present invention also relates to methods for producing 2-phenylethanol, and thus also pertains to methods for purifying 2-phenylethanol from mixtures containing other materials, such as methylbenzyl alcohol, benzyl alcohol, acetophenone, phenyl propanols, etc.

B. Alkylene Oxide-Styrene Monomer Production Processes

In one prior process for producing alkylene oxides, e.g., propylene oxide and styrene monomer, ethylbenzene is oxidized with air in a series of oxidizers to give a solution of ethylbenzene hydroperoxide in ethylbenzene. During this oxidation, some by-products are formed, notably methylbenzyl alcohol and acetophenone, and in minor amounts 2-phenylethanol and its precursors, e.g., 2-phenylethyl hydroperoxide. This solution of ethylbenzene hydroperoxide is then concentrated in successive steps of distillation, and unreacted ethylbenzene is recycled for oxidation.

Ethylbenzene hydroperoxide is then typically used to epoxidize the olefinically unsaturated compound, e.g., propylene, to propylene oxide, in the presence of a suitable catalyst. In this process, the hydroperoxide itself is converted to methylbenzyl alcohol. By-products of this reaction include more acetophenone, phenol, benzaldehyde, 2-phenylethanol, unreacted reactants, and high boiling materials.

Excess propylene in the aforementioned propylene oxide epoxidation product is normally removed by distillation. Propylene oxide may then be removed by distillation as a crude product, leaving a stream comprising excess ethylbenzene, the aforementioned by-products, and residues. The stream is then distilled to recover ethylbenzene overheads, leaving an aromatic rich distilland comprising methylbenzyl alcohol, acetophenone, and a variety of other by-products, including 2-phenylethanol. The composition of such distilland may vary widely and comprises a variety of alcohols, ketones and other by-products. (See Table I.)

In a typical propylene oxide-styrene monomer production process, the aforementioned methylbenzyl alcohol/acetophenone distilland (bottoms stream) is purified through distillation, and then is fed to styrene production reactors where it is contacted in the liquid phase with a suitable dehydration catalyst to convert methylbenzyl alcohol to styrene. After removing styrene from the dehydration reaction product by distillation, there is produced an acetophenone-rich bottoms product which is then hydrogenated using a suitable catalyst to convert acetophenone to methylbenzyl alcohol, which may then be recycled for styrene production.

Further information concerning the production of propylene oxide and styrene monomer are described in U.S. Pat. Nos. 3,403,193 (Russell) entitled "Process for the Co-Production of a Styrene and an Di-Olefin;" 3,4052,055 (Golden, et al) entitled "Process for the Recovery Epoxides Where an Alkylaromatic Compound is Removed in Two Distillation Zones," and 3,928,393 (Herzog) entitled "Process for the Preparation of Oxirane Compounds." In U.S. Pat. No. 3,403,193, for example, a styrene-diolefin production process similar to that described above is disclosed; from the following it will be seen that the present invention relates to the recovery of 2-phenylethanol from streams such as streams 9, 12, 15, 19, and more preferably 17, as disclosed in this patent.

In U.S. Pat. Nos. 3,526,674 (Becker, et al) entitled "Process for the Dehydration of Aralkanols," 3,442,963 (Korchak) entitled "Dehydration of Methyl Benzyl Alcohol to Styrene," 3,925,496 (Shalit, et al) entitled "Production of Styrene," 2,866,832 (Fenoglio, et al) entitled "Process for the Dehydration of Dimethylphenyl-carbinol" and 3,459,810 (Choo, et al) entitled "Process for the Preparation of Ethyl Benzene Hydroperoxide," other related production processes are disclosed, including processes which may be useful in the production of styrene through similar dehydration processes.

C. Prior 2-Phenylethanol Production Processes

Heretofore, 2-phenylethanol (-phenylethanol, phenylethyl alcohol, or phenylethyl alcohol, 2-phenylethyl alcohol benzylcarbinol) has generally been produced using any one of three commercially viable methods. Thus 2-phenylethanol has been produced commercially by using a Friedel-Crafts reaction of benzene and ethylene oxide (in the presence of aluminum trichloride) to produce primary yields in excess of about 90% 2-phenylethanol. The direct reduction of styrene oxide has also been utilized to produce primary yields of 2-phenylethanol in excess of about 90%. Such reductions are typically conducted by contacing catalysts, such as nickel, with hydrogen and styrene oxide to produce the aforementioned 2-phenylethanol product. A third commercially viable method for producing 2-phenylethanol involved the Grignard reaction of phenyl magnesium bromide with ethylene chlorohydrin. This method also results in primary yields of 2-phenylethanol which exceed about 90%.

Since the yields of the above-described methods are quite high, and the by-products of such processes are limited in number and amount, purification of such 2-phenylethyl alcohol products is relatively straightforward. When the aforementioned Grignard method is used to produce 2-phenylethyl alcohol, the major impurity in the reaction product which cannot be removed by simple distillation is diphenyl (biphenyl). U.S. Pat. No. 2,114,286, (which references British Pat. No. 398,561 of 1933) indicates that it is known to distill a crude Grignard reaction mixture to obtain a fraction consisting substantially of 2-phenylethyl alcohol and diphenyl, to then dissolve this fraction in benzene, treat it at room temperature with calcium chloride to form an insoluble 2-phenylethyl alcohol-calcium chloride double compound, separate the latter and wash the same with fresh benzene, then decompose the double compound with water, shaking the recovered alcohol with toluene, and finally distilling to recover the purified alcohol. U.S. Pat. No. 2,114,286 also discloses that some of the disadvantages associated with this procedure can be overcome by heating impure 2-phenylethyl alcohol containing diphenyl (or other impurities which do not react with calcium chloride) with anhydrous calcium chloride and an organic solvent to a temperature above 80° C., and then allowing the mixture to cool. A 2-phenylethyl alcohol-calcium chloride compound will then be obtained in the form of relatively large, well defined crystals which may be readily separated from the liquor by filtration and washed free of adherent impurities.

In U.S. Pat. No. 2,068,145 entitled "Purification of Alcohols," phenylethyl alcohol prepared by a Friedel-Crafts reaction of benzene with ethylene oxide in the presence of anhydrous aluminum chloride is disclosed as producing a product containing impurities, such as dibenzyl and phenylethyl chloride. While recognizing that the addition of calcium chloride has been suggested for purifying phenylethyl alcohol, such purification is described in U.S. Pat. No. 2,068,145 as being "not sufficiently complete." Instead, this patent discloses that phenylethyl alcohol should be treated with an acid which forms a sufficiently stable ester of sufficiently high boiling point so that the impurities may be distilled off. See also U.S. Pat. No. 2,052,881 (Klipstein) entitled "Purification of Alcohols."

In U.S. Pat. No. 3,579,593, the preparation of 2-phenylethyl alcohol is disclosed through the direct reduction of styrene oxide in the presence of two catalysts: Raney nickel and palladium. In U.S. Pat. No. 3,579,593 the use of these catalysts is disclosed as producing yields, based upon the amount of styrene oxide starting material, in excess of 95%, instead of 87–88% yields which may be realized by this process when other catalysts and catalyst mixtures are used. Under these circumstances, fractional distillation of the desired alcohol is disclosed as producing the desired 2-phenylethanol end product.

Other methods for purifying phenylethyl alcohol have also been suggested, and are often described as providing advantages over the method of purification involving the use of anhydrous calcium chloride which is said to be unsatisfactory in readily providing a pure product. See, for example, U.S. Pat. No. 1,752,365 which suggests the use of phthalic anhydride in such a purification.

In Japanese Patent Publication 1979-3026, published Jan. 11, 1979, entitled "A Method for Refining β-phenyl Ethyl Alcohol" (Tani, et al), a method is disclosed for refining 2-phenylethyl alcohol in which an addition product of 2-phenylethyl alcohol and a chloride, bromide or iodide of calcium, magnesium, manganese, or cobalt is formed. After this addition product is separated, 2-phenylethyl alcohol is recovered by dry distillation of said addition product under reduced pressure. After noting that the various methods for preparation of 2-phenylethyl alcohol include the three above-mentioned methods, Japanese patent states:

"In the β-phenylethyl alcohol obtained by these methods, however, various aromatic hydrocarbons or alcohols possessing aromatic radicals other than β-phenylethyl alcohol are present as impurities such as di-phenyl, di-benzyl, di-phenylmethane, 3-phenyl propanol, α-phenylethyl alcohol and -(2-hydroxy-ethoxy) ethylbenzene."

". . . by discovering that although β-phenyl alcohol easily forms an addition product with qualified metal halides, alcohols possessing an aromatic radical other than β-phenylethyl alcohol and aromatic hydrocarbon impurities either do not form any addition products at all or form additions that do not exceed a very small quantity."

Accordingly, this Japanese reference teaches such addition products should be formed using such a halide and a solvent which is inactive with respect to the appropriate metal halide and 2-phenylethyl alcohol. For the purpose, an aromatic hydrocarbon such as benzene or toluene, or other solvent such as a saturated hydrocarbon (hexane, pentane, or cyclohexane) solvent may be used which is subsequently separated from the addition product and recycled. In forming this addition product, this Japanese patent discloses that molar ratios of between 0.1:1 to 10:1 of metal halide compound to 2-phenylethyl alcohol may be used. After dry distillation, a 2-phenylethyl alcohol product having a purity in excess of 99.5%, and after simple rectification, with a purity of 99.9%, can be obtained. In support of its disclosure, Japanese Patent Publication 1979-3026 provides seven examples, each of which discloses the purification of crude 2-phenylethyl alcohol products which contain 2-phenylethyl alcohol weight percentages which are typical of those produced by the aforementioned conventional preparation procedures, i.e., crude products containing in excess of about 90% 2-phenylethanol.

In addition to the patents and publications referred to above, please refer to E. German Patentschrifts 112,116 (1975); 112,115 (1975); 112,114 (1975) and 112,643 (1975), as well as to U.S.S.R. Author's Certificate 123,955 entitled "Method for Separating Phenylethyl Alcohol" (Schumeyko, et al) (1959), which describe other methods for purifying 2-phenylethanol materials.

As seen from the above, most prior 2-phenylethanol production techniques rely on high primary yield processes which are followed by any one of the aforementioned purification methods. In these processes, the organic feed solutions from which 2-phenylethanol is separated almost invariably contain more than 90% 2-phenylethanol and less than about 10% by-products.

The principle behind the separation of organic mixtures by formation of metal complexes is discussed in an article entitled "Rapid Separation of Organic Mixtures by Formation of Metal Complexes," by K. Barry Sharpless, et al, *J. Org. Chem.* 40, 1252—1257 (1975). In this article, Dr. Sharpless notes that mixtures of organic alcohols have been purified for many years by the formation of complexes with calcium chloride and other anhydrous metal halides, however, for "unknown reasons" various metal complexing agents were generally less effective in separating compounds containing functional groups other than alcohols. Dr. Sharpless states:

"Our current understanding of the factors which determine selectivity is very limited. In general one must simply try this purification technique on the alcohol mixture in question to learn what the outcome will be. The empirical nature of this method should diminish as its use increases. In any case, we have observed certain effects which are worth pointing out. While discussing these factors individually, it is important to realize that although trends can be discerned for isolated factors, the actual effect on the selectivity is a complex function of all of the factors. Thus most of the following statements should be prefaced by the phrase 'other things being equal.'"

"More recently we have sought to establish an optimum set of reaction conditions to be tried first on any new mixture. The factors to be optimized are, of course, selectivity and the recovery—the product of these two determines the yield of the desired component isolated from the mixture. Unfortunately, this has not been easy, since *each mixture*

*seems to respond differently to the controllable variables.*" (emphasis added) (at page 1253)

Thus while the art discloses that certain of the reaction mixtures containing more than about 90% 2-phenylethyl alcohol can be successfully complexed with metal halides, Sharpless teaches that such results do not predict whether 2-phenylethanol can be separated by this method from solutions having markedly different compositions.

SUMMARY OF THE INVENTION

The present invention provides a novel method for producing 2-phenylethanol by oxidizing ethylbenzene to produce very minor proportions of 2-phenylethanol and its precursors in an ethylbenzene hydroperoxide process stream. More particularly, 2-phenylethanol is recovered from the subject process stream after ethylbenzene hydroperoxide has been reacted with an olefin to produce a mixture of products including minor proportions of 2-phenylethanol. Although 2-phenylethanol is not normally present in this mixture in proportions which permit its recovery directly from the process stream, it has been found that by adjusting the composition of said mixture, in particular, the proportion of methylbenzyl alcohol, metal halide complexing of 2-phenylethanol is facilited so that its removal from a mixture predominantly composed of methylbenzyl alcohol and acetophenone is possible. The metal halide-2-phenylethanol insoluble adduct thus formed is then separated from the remainder of the mixture and eventually decomposed to provide a high purity 2-phenylethanol product.

A relatively simple method is thus provided for recovering 2-phenylethanol from a typical alkylene oxide/styrene monomer process stream, which 2-phenylethanol would otherwise reduce styrene production and largely be purged with other by-products for disposal or use as fuel.

Accordingly, a primary object of the present invention is the provision of a novel method for producing high purity 2-phenylethanol.

A further object of the present invention is the provision of a method for recovering 2-phenylethanol from an olefin oxide/styrene monomer process stream.

A further object of the present invention is the provision of a novel method for refining a mixture which may contain substantial proportions of methylbenzyl alcohol and minor proportions of 2-phenylethanol.

These and other objects of the present invention will become apparent from the following more detailed description.

BRIEF DESCRIPTION OF THE DRAWINGS

FIG. 1 is a simplified block diagram of a conventional propylene oxide/styrene monomer process;

FIG. 2 is a flow chart of the preferred method of the present invention showing the separation of high purity 2-phenylethanol from a process stream, such as stream 114, stream 115, or stream 116 of FIG. 1;

FIG. 3 is a graph showing the effect of complexation feed composition on selectivity, and illustrating the preferred range of 25–70% 2-phenylethanol in the feed;

DETAILED DESCRIPTION OF THE PREFERRED EMBODIMENTS

While specific examples have been selected for purposes of illustration in the following description, one of ordinary skill in the art will recognize that various departures can be made from the materials and methods disclosed hereinafter without departing from the scope of the present invention, which is defined more particularly in the appended claims.

As may be used herein, the terms "methylbenzyl alcohol," "MBA," "-phenylethanol," and "-MBA" are intended to refer to 1-phenylethanol and the term, "2-PE," is intended to refer to 2-phenylethanol.

The present invention provides a novel method for producing and recovering a substantially pure 2-phenylethanol product having superior fragrance qualities from liquid solutions containing complex admixtures comprised of aromatic hydrocarbons and oxygenated derivatives thereof. One convenient source of such an admixture is the epoxidation reaction product obtained in the process for the coproduction of an alkylene oxide and styrene monomer by the process involving: oxidizing ethylbenzene to produce an ethylbenzene hydroperoxide product containing less than about 20, and generally less than about 5, weight percent of 2-phenylethanol and its precursors; reacting that ethylbenzene hydroperoxide with an olefin to produce an epoxidation reaction product ("epoxidate") comprising primarily an oxirane compound, methylbenzyl alcohol, acetophenone, and minor amounts, of 2-phenylethanol; and separating the oxirane compound, unreacted olefin, and ethylbenzene from said reaction product to produce an aromatic rich distilland comprised of said residual compounds.

In accordance with one aspect of the present invention, the content of the aforementioned aromatic rich distilland is adjusted to produce a feedstock containing between about 20 and 80, preferably between 25 and 70, weight percent, of 2-phenylethanol, and between about 10 and 70, preferably between 30 and 60, weight percent, methylbenzyl alcohol; diluting this adjusted stream with an organic diluent to form a complexation feed solution, and compexing this feed solution through the addition of a metal halide to produce an insoluble metal halide-2-phenylethanol adduct. The adduct is finally separated and washed, and then decomposed to recover 2-phenylethanol, preferably by displacement with sufficient water to form a multiple phase liquid product comprising at least one 2-phenylethanol containing organic layer. A final high purity 2-phenylethanol product is then recovered from said organic layer, preferably by distillation. The "epoxidate" starting material of the recovery process of the present invention, in general, is obtained in accordance with the procedure set forth in U.S. Pat. No. 3,351,635; U.S. Pat. No. 3,403,193, U.S. Pat. No. 3,405,055; and U.S. Pat. No. 3,928,393, the disclosures of which are hereby incorporated by reference.

In the event the aforementioned aromatic-rich distilland product contains substantial quantities, i.e., greater than about 5 weight percent, of high boiling components having boiling points above about 235° C., it is necessary to remove such products prior to complexing in accordance with the process of the present invention, to preclude the formation of undesired tar-like masses upon the addition of metal halide to the complexation feed solution. Hence, under these circumstances, the adjustment of the contents of the aromatic-rich distilland product would further comprise separation of such high boiling components, i.e., by distillation, thereby resulting in a distillate product which is suitable for use as a starting material feed in the process of the present invention. It is to be understood that the percentages of this feedstock referred to in this specification and claims are on a high boiling component-free basis.

In general, any metal halide capable of complexing 2-phenylethanol may be employed in the process of the present invention. Illustrative metal halides employable include the alkaline earth metal halides such as those of calcium, magnesium, and barium, as well as halides of other divalent metals such as manganese, cobalt, zinc, and nickel. Although any metal halide may be used in this invention, for example, the chloride, bromide, fluoride or iodide, of any of the aforementioned metals, the preferred metal halide is calcium chloride. The metal halide employed in the process of the invention is substantially anhydrous to ensure complexing capability of the metal halide with 2-phenylethanol. The metal halide to 2-phenylethanol molar ratio employed in the process is not critical, and generally may range from about 0.1 to 10, preferably from 0.5 to 1.5. Hereinafter, the metal halide may be referred to as calcium chloride; but it is to be understood that any such metal halide is intended where calcium chloride is mentioned.

Suitable diluents employable in the process of the present invention should be inert to and not complex with, the aforementioned metal halide. In addition, the diluent should be incapable of substantially solubilizing the metal halide: 2-phenylethanol complex to be formed, and, as such, should permit formation of a slurry of the complex in the diluent. Specific examples of diluent which may be employed in the process of the present invention are aromatic hydrocarbons, such as benzene or alkyl substituted derivatives thereof, illustratively toluene and ethylbenzene; aliphatic hydrocarbons containing from about 5 to 20, preferably 5 to 8, carbon atoms, illustrated by hexane, octane, heptane, etc., as well as halogenated hydrocarbons, such as chlorobenzene, carbon tetrachloride, and the like. The diluent to complexation feed solution weight ratio may vary widely and generally will range between about 1 to 30, and preferably between about 3 to 10.

In general, reaction conditions employed in the formation of the 2-phenylethanol: metal halide complex are not critical. It has been found that complexation may be conveniently conducted at temperatures ranging between about 0° and 100° C., preferably between 20° and 40° C., with contact times of at least 10 minutes, and preferably between 30 minutes and 2 hours, providing desirable results.

FIG. 1 is a block diagram of a portion of a propylene oxide/styrene monomer process. One of ordinary skill in this art will recognize that FIG. 1 is a simplified flow chart of a portion of a production process similar to that disclosed in U.S. Pat. No. 3,403,193, wherein methylbenzyl alcohol ("MBA") dehydration block 104 and acetophenone ("ACP") hydrogenation block 106 correspond to steps 18 and 27 of U.S. Pat No. 3,403,193. Similarly, the oxidation/epoxidation block 100 of FIG. 1 corresponds to steps 1, 3, 7, 10 and 13 of U.S. Pat. No. 3,403,193, while the MBA stripper bottoms stream 117 corresponds to purge stream 20 of this patent. Maximum concentration of 2-phenylethanol present in this system are found in streams 115, 116, and 114. Due to recycling of materials within the system, a major proportion of the 2-phenylethanol resulting from the oxidation/epoxidation step 100 eventually reacts with styrene precursors to form high boiling compounds in methylbenzyl alcohol dehydration, thereby resulting in lower styrene yields. Thus recovery of 2-phenylethanol not only yields a valuable product, but also increases styrene yields in the above described system.

While concentrations of 2-phenylethanol are not found in the illustrated process which would otherwise interfere with overall process operation, processes which do not convert or consume 2-phenylethanol may experience undesirable buildups of 2-phenylethanol within the system which may be unacceptable in commercial operation. For example, increases in 2-phenylethanol concentrations may adversely affect catalysts which are used in the dehydration or hydrogenation reactions. Accordingly, preferred removal of 2-phenylethanol from such as process stream enables a greater flexibility in the design and/or operation of the remaining portions of the system.

It is presently preferred to employ the methylbenzyl alcohol stripper distillate stream 115 of FIG. 1 as the primary 2-phenylethanol containing solution due to its relatively high 2-phenylethanol concentration, and since it is "up stream" of dehydration. Table I provides a listing of the ranges of weight percents of typical components found in such a stream:

TABLE I

| Component | wt. % |
|---|---|
| Lights (B.P. below about 175° C. at atm. pressure) | <5 |
| Phenol | <1 |
| Phenylacetaldehyde and 2-Phenyl-Propionaldehyde | <1 |
| Acetophenone | <25 |
| MBA | >10 |
| Benzyl Alcohol | <5 |
| 1-Phenyl-1-Propanol | <5 |
| Cumyl Alcohol (2-Phenyl-2-Propanol) | <5 |
| Phenyl Propanones | <5 |
| 2-Phenylethanol | <20 |
| 2-Phenyl-2-Propanol | <10 |
| 2-Phenyl-1-Propanol | <5 |
| 1-Phenyl-2-Propanol | <5 |
| 1-Phenylethyl Acetate | <5 |
| 2-Ethylphenol | <10 |
| Hydroxymethyl Tetralin ($C_{11}H_{14}O$) Isomers | <5 |
| Methyl Naphthalene Isomers | <5 |
| 3-Phenyl-1-Propanol | <10 |
| Heavies (B.P. above about 235° C. at atm. pressure) | <20 |

As shown from the following examples, the process stream of Table I may not be readily purified to obtain 2-phenylethanol of high purity using any given conventional purification procedure

EXAMPLE 1

Each distillation of a sample conforming to the composition of the stream of Table I was conducted to determine whether distillative purification of that stream to produce pure 2-phenylethanol was possible. This distillation was effected under a pressure between 5–10 mm Hg at 20:1 reflux ratio in a B/R 36T spinning band distillation column which, under the operating condiditions employed, had about 80 theoretical plates. The distillate fraction richest in 2-phenylethanol contained 80 weight percent 2-phenylethanol. The balance consisted of compounds having boiling points approximating the boiling point of 2-phenylethanol, including phenyl propanol isomers, hydroxymethyl tetraline ($C_{11}H_{14}O$) isomers, methyl naphtalene isomers, 2-ethylphenol, phenyl propanone isomers, 1-phenylethyl hexyl ethers, 1-phenylethyl acetate, and several other unidentified trace impurities. From these results it was concluded that distillation is not a feasible approach to the purification of 2-phenylethanol from such a complex process stream.

EXAMPLE 2

Experiments were conducted which included cooling the overhead batch distillation heartcut of Example 1, consisting of 80 weight percent 2-phenylethanol, which resulted in the formation of a glassy solid which occluded all impurities. It was thus concluded that crystallization from melt was not a feasible approach to the separation of 2-phenylethanol from this process stream.

The preferred embodiment method for removing 2-phenylethanol from stream 115 of FIG. 1 is diagramatically illustrated in FIG. 2. In accordance with the preferred embodiment of the present invention, applicants have recognized that process stream feeds, such as those described in Table I, do not contain sufficient amounts of 2-phenylethanol to permit separation of 2-phenylethanol from the remainder of the mixture through any single separation technique. The concentration of 2-phenylethanol in the process stream 115 of FIG. I is typically less than about 20%, and often below about 10%, as illustrated in Table I. The following examples were thus performed

EXAMPLE 3

In order to study the effect of methylbenzyl alcohol concentration on complexation of 2-phenylethanol with metal halides, various feeds were obtained by combining distillate fractions from laboratory batch distillations of a process stream sample conforming to that set forth in Table I, so as to span a wide range of 2-phenylethanol and methylbenzyl alcohol concentrations. The result of these combinations are set forth in Table II, wherein the various experimental solutions are designated with letters A-E.

TABLE II

COMPOSITION OF COMPLEXATION FEED SOLUTIONS (Wt %)

| Component | Solution Designation | | | | |
|---|---|---|---|---|---|
| | A | B | C | D | E |
| 1-Phenylethyl Hexyl Ether | 1.52 | 1.31 | 1.10 | 0.63 | ND |
| Phenylacetaldehyde or 2-Phenyl-Propionaldehyde | 0.99 | 0.57 | 0.14 | 0.08 | ND |
| Acetophenone | 0.48 | 0.73 | 0.97 | 0.55 | ND |
| 1-Phenylethyl Acetate | 0.25 | 0.29 | 0.32 | 0.18 | ND |
| Phenyl Propanones | 0.58 | 0.56 | 0.53 | 0.30 | ND |
| $C_{11}H_{14}O$ Isomers | 8.18 | 8.08 | 7.98 | 4.56 | ND |
| Cumyl Alcohol | 1.26 | 0.99 | 0.72 | 0.41 | ND |
| MBA | 4.66 | 14.73 | 24.79 | 57.02 | 75 |
| 1-Phenyl-2-Propanol | 1.92 | 1.85 | 1.78 | 1.02 | ND |
| Benzyl Alcohol | | | 1.10 | 0.63 | ND |
| 1-Phenyl-1-Propanol | 0.92 | 1.26 | 0.50 | 0.29 | ND |
| 2-PE | 66.48 | 54.65 | 42.81 | 24.46 | 10 |
| 2-Phenyl-1-Propanol | 7.61 | 9.50 | 11.38 | 6.50 | ND |
| 2-Ethyl-Phenol | 1.23 | 1.04 | 0.84 | 0.48 | ND |
| Unknowns | 3.92 | 4.44 | 5.01 | 2.89 | ND |

Using the experimental solutions of Table II, metal halide complexes were formed by first diluting the solution indicated with 12 ml. of hexane per gm. of solution, then adding 80 mesh substantially anhydrous calcium chloride at an equimolar amount with 2-phenylethanol, and stirring the resulting slurry at 22° C. for 2 hours. Following separation by filtration of the insoluble complex formed, the recovered complex was repeatedly washed with about 6-8 volumes of pentane. Thereafter, the washed complex was decomposed in a laboratory dryer at about 165° C. under vacuum (3-5 mm Hg.) and the desired 2-phenylethanol, reulting therefrom, was recovered. The results of these studies are set forth in Table 3 and graphically depicted in FIG. 3.

TABLE III

Effect of Methylbenzyl Alcohol on the Selectivity of 2-Phenylethanol Complexation

| Impure 2-PE Solution | 2-PE Complexed, % | Purified 2-PE Analysis wt % | |
|---|---|---|---|
| | | 2-PE | MBA |
| A | 76 | 99.93 | 0.04 |
| B | 73 | 99.83 | 0.15 |
| C | 60 | 99.41 | 0.52 |
| D | 78 | 99.68 | 0.30 |
| E | Not determined | 25.00 | 58.9 |

As is evident from FIG. 3, these studies indicate that the complexation technique may be applied to materials containing no less than about 20 weight percent 2-phenylethanol, and as much as about 70 weight percent methylbenzyl alcohol, with very little penalty on the purity of the end product. The major impurity in the 99+ percent 2-phenylethanol, in all cases, was methylbenzyl alcohol.

EXAMPLE 4

In accordance with the method of the present invention, the crude 2-phenylethanol feed material is diluted with an organic diluent prior to complexing. In order to investigate the effect various organic diluents may have on the purity of the desired 2-phenylethanol product, tests were conducted comparing the selectivity obtained using hexane and ethylbenzene diluents. In these experiments, complexation took place at 22° C., over a two hour contact time, using 12 ml of diluent per gram of solution A (Table II) and a 1:1 calcium chloride to 2-phenylethanol molar ratio. For these experiments less than 80 mesh substantially anhydrous calcium chloride was used, washing was conducted six times with 2.5 ml of the specified diluent per gram of solution A, and the formed complex was decomposed by dry distillation, as disclosed in Example 3. The recovered 2-phenylethanol product which contained trace amounts of diluent, was then distilled using a B/R 36T spinning band column under 5-15 mm Hg overhead pressure and at 200:1 reflux ratio. The compositions of purified 2-phenylethanol are set forth in Table IV:

TABLE IV 2-phenylethanol Purified with Hexane or Ethylbenzene Diluent

| | Composition, wt % | | | |
|---|---|---|---|---|
| | Before Finishing Distillation | | After Finishing Distillation | |
| | Hexane | Ethylbenzene | Hexane | Ethylbenzene |
| Ethylbenze or Hexane | 0.005 | 0.014 | 0 | 0 |
| Phenylacetaldehyde | 0.013 | 0.011 | 0 | 0 |
| Acetophenone | 0.009 | 0.008 | 0.005 | 0.005 |
| Phenyl Propanones | 0.004 | 0 | 0 | 0 |
| $C_{11}H_{14}O$ Isomers | 0.005 | 0 | 0.005 | 0 |
| MBA | 0.046 | 0.026 | 0.020 | 0.009 |
| 1-phenyl-2-propanol | 0.055 | 0.021 | 0.042 | 0.019 |
| Benzyl Alcohol and/or 1-phenyl-1-propanol | 0.012 | 0 | 0.007 | 0 |
| 2-PE | 99.703 | 99.882 | 99.767 | 99.935 |
| 2-phenyl-2-propanol | 0.148 | 0.035 | 0.148 | 0.032 |
| 2-ethyl-phenol | 0.005 | 0 | 0.006 | 0 |
| Unknown | 0 | 0.003 | 0 | 0 |

As is evident from the results of Table IV, 2-phenylethanol product of exceedingly high purity may be obtained by the process of the present invention. When evaluated by fragrance experts, the ethylbenzene purified material exhibited fragrance qualities superior to commercially available 2-phenylethanol product.

Referring again to FIG. 2, following the formation of the aforementioned insoluble complex at step 202, the complex is separated from the liquid effluent and is then washed with clean diluent at separation and washing step 204. The thus obtained liquid effluent primarily comprises diluent such as ethylbenzene, methylbenzyl alcohol, acetophenone, 2-phenyl-1-propanol, the other minor components which were present in the feed solution. In accordance with the preferred method of the present invention, the major components of the effluent stream may be recycled to other portions of the oxirane compound/styrene monomer production system. For example, the complex wash effluent may be separated to remove ethylbenzene therefrom which may be recycled for reuse as a diluent, or as feedstock for oxidation step 100 (FIG. 1). The remaining portion of the complexation liquid effluent, comprising primarily methylbenzyl alcohol and acetophenone, may be transferred to methylbenzyl alcohol dehydration step 104 and acetophenone hydrogenation step 106.

In accordance with of the present invention, the preferred method to effect complex decomposition 206 is by displacement of 2-phenylethanol with water, although dry distillation under vacuum may be used, as is evident from the examples. Displacement of 2-phenylethanol with water is preferred because it is simple and unlikely to result in the decomposition of 2-phenylethanol. Preferably, water is added directly to the washed, diluent wet complex. In general, sufficient water is employed to produce a nearly saturated metal halide solution. Separation between the aqueous and organic phases is readily accomplished, particularly when certain aromatic diluents, such as ethylbenzene are employed. It is also feasible, but much less preferred, to add just enough water to form a mixture of crystalline metal halide hydrates, which can be separated from the 2-phenylethanol/ethylbenzene solution by gravity sedimentation. The hydrates will, however, be wetted with organics and would require drying before further processing. After complex decomposition 206, the 2-phenylethanol product thus obtained may be distilled in conventional manner as shown in step 208, to obtain a highly pure product exhibiting superior fragrance qualities, containing less than 100 ppm acetophenone and less than about 0.5 weight percent methylbenzyl alcohol, and, when ethylbenzene is employed as diluent, less than 100 ppm ethylbenzene. Accordingly, the preferred method of the present invention provides a novel method for producing high purity, commercially acceptable 2-phenylethanol.

What is claimed is:

1. A method for the recovery of 2-phenylethanol from an aromatic-rich distilland product obtained from the process for the production of an oxirane compound by the oxidation of ethylbenzene to produce an ethylbenzene hydroperoxide product mixture, reacting said ethylbenzene hydroperoxide product mixture with an olefinically unsaturated compound to produce an epoxidation reaction product comprising primarily said oxirane compound, acetophenone, methylbenzyl alcohol and up to about 20 weight percent of 2-phenylethanol and separating said oxirane compound and unreacted reactants from said reaction product, thereby obtaining said aromatic-rich distilland product, said method comprising:
   (a) adjusting the composition of said distilland product to produce a feedstock comprising about 20 to 80 weight percent 2-phenylethanol and about 10 to 70 weight percent methylbenzyl alcohol;
   (b) diluting the product obtained in step (a) with an organic diluent in an amount sufficient to produce a complexation feed solution, said diluent being inert to and not capable of complexing with the initial halide employed in step (c) below;
   (c) forming an insoluble metal halide-2-phenylethanol adduct by contacting said complexation feed solution with a substantially anhydrous metal halide;
   (d) separating said adduct from said solution; and
   (e) decomposing said adduct to obtain a 2-phenylethanol product.

2. The method of claim 1 wherein said olefinically unsaturated compound is propylene.

3. The method of claim 1 wherein adjustment of the composition of said distilland product is effected by further distillation.

4. The method of claim 1 wherein said organic diluent is a hydrocarbon.

5. The method of claim 1 wherein the metal of said metal halide is divalent.

6. The method of claim 5 wherein said divalent metal halide is calcium chloride.

7. The method of claim 1 wherein said adduct is washed with an organic solvent following separation.

8. The method of claim 4 wherein said diluent is ethylbenzene.

9. The method of claim 7 which said solvent is ethylbenzene.

10. The method of claim 9 wherein said ethylbenzene wash liquor is recovered and recycled to said oxidation.

11. The method of claim 7 wherein said 2-phenylethanol-metal halide adduct is decomposed by displacing 2-phenylethanol with water to form a multiple phase liquid product comprising at least one 2-phenylethanol containing organic layer.

12. The method of claim 11 wherein said 2-phenylethanol containing layer is distilled to produce a high purity 2-phenylethanol product containing less than 100 ppm ethylbenzene, less than 100 ppm acetophenone, and less than about 0.5 weight percent methylbenzyl alcohol.

13. The method of claim 1 wherein said adjustment step further comprises separating sufficient high boiling point materials from said distilland product to prevent the formation of undesired tar-like masses upon the contacting of the of metal halide with the complexation feed solution.

14. The method of claim 1 wherein the product obtained in step (a) is diluted with at least about 3 parts, by weight, of organic diluent per part of feedstock.

15. The method of claim 1 wherein the distilland product of step (a) is adjusted to produce a feedstock comprising about 25 to 70 weight percent 2-phenylethanol and about 30 to 60 weight percent methylbenzyl alcohol.

16. A method for the recovery of 2-phenylethanol from an aromatic-rich distilland product obtained from the process for the production of propylene oxide by the oxidation of ethylbenzene to produce an ethylbenzene hydroperoxide mixture, reacting said ethylbenzene hydroperoxide mixture with propylene to produce an epoxidation reaction product comprising primarily propylene oxide, acetophenone, methylbenzyl alcohol and up to about 20 weight percent of 2-phenylethanol and separating propylene oxide and unreacted reactants from said reaction product, thereby obtaining said aromatic-rich distilland product, said process comprising:

(a) subjecting said distilland product to further distillation to produce a feedstock comprising about 25 to 70 weight percent 2-phenylethanol and about 30 to 60 weight percent methylbenzyl alcohol;

(b) diluting the product obtained in step (a) with at least about 3 parts, by weight, of ethylbenzene per part of feedstock to produce a complexation feed solution;

(c) contacting said complexation feed solution with substantially anhydrous calcium chloride to produce an insoluble calcium chloride-2-phenylethanol adduct;

(d) separating said adduct from said solution;

(e) washing said separated adduct with ethylbenzene following separation;

(f) decomposing said adduct by displacing 2-phenylethanol with water to form a multiple phase liquid product comprising at least one 2-phenylethanol-containing organic layer; and (g) distilling said 2-phenylethanol-containing layer to produce a high purity 2-phenylethanol product containing less than 100 ppm ethylbenzene, less than 100 ppm acetophenone and less than about 0.5 weight percent methylbenzyl alcohol.

* * * * *